(12) United States Patent
Larkin et al.

(10) Patent No.: US 7,027,138 B2
(45) Date of Patent: Apr. 11, 2006

(54) ENHANCED SENSITIVITY DIFFERENTIAL REFRACTOMETER INCORPORATING A PHOTODETECTOR ARRAY

(75) Inventors: Michael I. Larkin, Santa Barbara, CA (US); Steven P. Trainoff, Goleta, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 0 days.

(21) Appl. No.: 10/961,633

(22) Filed: Oct. 7, 2004

(65) Prior Publication Data

US 2005/0168726 A1 Aug. 4, 2005

Related U.S. Application Data

(63) Continuation-in-part of application No. 10/768,600, filed on Jan. 29, 2004, now Pat. No. 6,975,392.

(51) Int. Cl.
*G01N 21/41* (2006.01)
(52) U.S. Cl. .................. 356/128; 356/130; 356/246; 356/73; 250/237
(58) Field of Classification Search ........ 356/128–137, 356/73, 246; 250/237
See application file for complete search history.

(56) References Cited

U.S. PATENT DOCUMENTS

| | | | | |
|---|---|---|---|---|
| 3,386,332 A | * | 6/1968 | Watson | 356/130 |
| 3,539,263 A | * | 11/1970 | Waters | 356/130 |
| 3,680,963 A | * | 8/1972 | Edwards et al. | 356/517 |
| 4,276,475 A | * | 6/1981 | Nelson | 250/373 |
| 4,952,055 A | * | 8/1990 | Wyatt | 356/73 |
| 5,129,723 A | * | 7/1992 | Howie et al. | 356/336 |
| 5,157,454 A | * | 10/1992 | Oka et al. | 356/130 |
| 5,201,220 A | * | 4/1993 | Mullins et al. | 73/152.42 |
| 5,305,071 A | * | 4/1994 | Wyatt | 356/73 |
| 5,305,073 A | * | 4/1994 | Ford, Jr. | 356/338 |
| 5,483,344 A | * | 1/1996 | Frot et al. | 356/484 |
| 2005/0110982 A1 | | 5/2005 | Larkin | |
| 2005/0168733 A1 | | 8/2005 | Larkin | |

OTHER PUBLICATIONS

A. E. Einstein, "The Theory of the opalescence of homogeneous fluids and liquid mixtures near the critical state," Annalen der Physik, 1910, pp. 1275-1298, vol. 33, Germany.
E. Hecht, Optics Second Edition, 1987, pp. 401-406, Addison-Wesley, Reading, United States of America.

* cited by examiner

*Primary Examiner*—Samuel A. Turner
*Assistant Examiner*—Sang H. Nguyen
(74) *Attorney, Agent, or Firm*—Philip J. Wyatt

(57) ABSTRACT

An improved differential refractometer incorporating a photodetector array is disclosed. Using a multi-element photo array provides the basis for measurement of differential refractive index values with a heretofore unattainable combination of sensitivity of measurement and concurrent range of measurement. Within the large dynamic range attainable, the detector structure provides equal sensitivity irrespective of deflection within the range. The transmitted light beam is tailored to provide a spatial variation of the light intensity at the array improving thereby the precision of measurement of its displacement. This in turn results in improved precision in the reported differential refractive index and in the calculation of the differential refractive index increment dn/dc. Integrating the detector array into the flow cell structure of the parent case results in a detector of exceptional sensitivity and range for sample quantities far smaller than required by conventional differential refractometers.

39 Claims, 12 Drawing Sheets

ENHANCED SENSITIVITY DIFFERENTIAL REFRACTOMETER INCORPORATING A PHOTODETECTOR ARRAY

CONTINUATION-IN-PART

This application is a continuation-in-part of Ser. No. 10/768,600 filed 29 Jan. 2004 now U.S. Pat. No. 6,975,392, M. Larkin, "Enhanced Sensitivity Differential Refractometer Measurement Cell"

RELATED AND OTHER CO-PENDING APPLICATIONS

Expressly incorporated herein are the following related patents and concurrent applications. These are of importance as the present invention insures that they may be used and implemented more effectively:

Ser. No. 10/723,548 filed 25 Nov. 2003, M. Larkin, "Refractometer Cell for both Absolute and Differential Refractive Index Measurement of Fluids."

U.S. Pat. No. 4,616,927—"Sample Cell for Light Scattering Measurements," (Oct. 14, 1986)

U.S. Pat. No. 5,530,540—"Light scattering measurement cell for very small volumes," (25 Jun. 1996)

U.S. Pat. No. 6,411,383—"Method for measuring the $2^{nd}$ virial coefficient," (25 Jun. 2002).

U.S. Pat. No. 6,651,009—"Method for determining average solution properties of macromolecules by the injection method," (Nov. 18, 2003)

Ser. No. 10/665,903 filed 18 Oct. 2003, S. Trainoff, "Method for Correcting the Effects of Interdetector Band Broadening."

Ser. No. 10/768,600 filed 29 Jan. 2004, M. Larkin. "Enhanced Sensitivity Differential Refractometer Measurement Cell."

BACKGROUND

The difference in refractive index between a sample and a reference material is referred to as the differential refractive index, dRI, and is a physical parameter of considerable importance. The dRI between a sample solution consisting of a solvent plus a solute and a reference solution comprised of a pure solvent may be used to determine the solute concentration from the relation $$\Delta c \approx \Delta n / \left(\frac{dn}{dc}\right),$$

where the change in concentration, $\Delta c$, is directly proportional to the measured change in solution refractivity, $\Delta n$. The constant of proportionality is the reciprocal of the differential refractive index increment, $$\frac{dn}{dc}.$$

A typical instrument for measuring the dRI is a "walk-off" type differential refractometer. That instrument contains a cell made of a transparent material with two fluid chambers, able to accommodate either a liquid or a gas, and having an angled transparent interface separating the chambers. As pictured in FIG. 1, a beam of light 1 passes into the cell, through sample chamber 2, through the interface 3 separating the two chambers, through reference chamber 4, and finally out of the cell. For the cell pictured, if the fluids in the two chambers have identical indices of refraction, then after exiting the cell the transmitted beam of light 5 travels in a path parallel to the incident beam 1. If the two fluids have different indices of refraction, then the transmitted beam of light 6 travels in a path which is at some angle θ to the incident beam. The angle θ between the incident light beam and the transmitted light beam is, to first order, proportional to the difference in refractive index between the two liquids. That angular deflection of the light beam may be measured by a variety of well established techniques, and so the dRI may be measured and reported.

The measured differential refractive index increment, $$\frac{dn}{dc},$$

is generally a function of the wavelength of the illuminating light beam. This quantity plays a major role in calculating the sample concentration for a light scattering measurement used to determine the molar mass and size of such samples. For such use with light scattering measurements, the wavelength of the refractometer beam is chosen the same as that used in the light scattering photometer. For a monochromatic beam, the differential refractometer light source may be selected as a light emitting diode, a laser, or even a white light source combined with a narrow band pass filter. Some differential refractometers use a white light source providing thereby an averaging over a range of $$\frac{dn}{dc}$$

values.

Although the incident beam, as shown in FIG. 1, strikes the sample chamber interface normal to the entrance surface, in general, the incident beam will be oriented at an angle to it. In this manner, for example, it becomes possible to have the finally transmitted beam reflected by a mirror back into the flow cell chambers so that the beam exits through the same surface. By such mirror means the sensitivity of the cell will be doubled. The emerging beam will not be parallel to or co-linear with the incident beam and may be detected more easily.

Conventionally, the angle of the transparent interface between sample and reference chambers is of the order of 45° with respect to the direction of the incident beam, though the greater this angle is the greater will be the angular deflection of the transmitted beam due to the difference between refractive indices of the sample and reference fluids. For the geometry shown, increasing this angle results in a requirement for a sample fluid chamber of increased volume while decreasing it decreases the angular deflection due to the refractive index difference between the sample and reference fluids For many applications, sample preparation requires a great expenditure of time and resources, and reducing the quantity of sample required for measurements has a direct benefit. In addition to a reduction the effort associated with sample preparation, the quality of measurements is enhanced if the quantity of sample required for a measurement is reduced. Liquid chromatographic systems are one example where the quality of the measurements is improved if the volume of sample required for measurement is reduced. In a liquid chromatographic system a material potentially consisting of many species is dissolved into a solvent and then injected into a fluid stream. The fluid stream is made to traverse some medium or device which preferentially delays species in the medium or device based upon some physical parameter, such as size, chemical affinity, thermal properties, electrical properties, etc., and so separates the species from one another. The different species thus exit the medium or device at different times. In keeping with traditional nomenclature, this medium or device will here be referred to as a column, although the physical form and function of the device may be quite different from a column. The fluid passing through the column typically exits into a small diameter tube, and so at any one moment in time different species reside at different locations along the length of the tube. If a measurement device, such as a differential refractometer, is situated such that the fluid flows from that tube through the measurement device, then the species which make up the material may be individually measured. The measurement of constituent species of a material is an essential purpose of chromatographic systems. Since a finite volume of liquid is always required for measurement, the species within some volume of the tube necessarily contribute to the signal at any moment in time. The measurement device is therefore always measuring an average over the species which reside along the length of the tube which corresponds to the measurement volume. This averaging over species negates in part the separation accomplished by the column, and results in a reduction in the quality of data. Reducing the volume of sample required for measurement minimizes the averaging over species, resulting in higher quality data.

In addition to the negative effects on data quality due to the measurement averaging over a finite volume of sample, some volume of sample is mixed together as it traverses the measurement system. Many chromatographic systems consist of several measurement devices placed serially along the fluid stream, each measuring different physical parameters concerning the sample. If a measurement device mixes some volume of fluid together, then all subsequent measurements on that fluid are negatively impacted by the resulting averaging over multiple species in the measurement volume. Typically, the larger the volume required for measurement, the larger the volume of sample which is mixed together, and the greater the negative impact on data quality for instruments placed later in the fluid stream.

In addition to their application in the field of liquid chromatography, differential refractometers of various types are used in many different fields. By accurately determining refractive index differences between a reference standard and a sample, such determinations may be used to determine sucrose concentration, fluid densities, the concentrations of a myriad of industrial fluids such as sulfuric acid, sodium chloride, ethanol, etc. A variety of instruments have been designed around the concept of measuring and using such refractive index differences as a means to measure various derivative quantities.

There are clearly advantages in reducing the volume of sample required for a dRI measurement. However, for a walk-off type differential refractometer, a tradeoff exists between reduction of the sample volume and sensitivity of the dRI measurements. There are at least three reasons for a reduction in dRI sensitivity with a reduction in sample volume. The first reason for a reduction in sensitivity is a reduction in averaging over the sample. For even perfectly stable systems, fundamental laws of thermodynamics predict local fluctuations through time of the temperature, density, and solute concentrations across the sample and reference liquids. This was explained at length by Albert Einstein in his 1910 seminal paper on "The theory of opalescence of homogeneous fluids and liquid mixtures near the critical state," published in *Annelen der Physik*, volume 33, pages 1275–1298. Real world systems are never perfectly stable, and those fluctuations are in general enhanced in real systems. Those fluctuations cause the path of the light beam traversing the fluids to change through time, and so cause the angle $\theta$ at which the light beam 6 exits the cell to fluctuate with time. The fluctuations through time of the beam angle are seen as noise in the dRI measurement. Increasing the volume sampled by the beam causes the beam to better average over these local fluctuations, reducing their overall effect.

A second reason that a reduction in sample volume results in a reduction in sensitivity of the dRI measurement is a reduction of optical power through the system. For the cell design picture in FIG. 1, as the sample volume is reduced, the area of sample through which light may be sent is reduced. To obtain the same optical power through the system, the light intensity must be increased. Typically, a system used to measure the angular deflection of the light beam has its sensitivity increase in some proportion to the optical power supplied to it. Therefore, to obtain with a smaller volume sample the same sensitivity in the determination of the beam angular deflection as with a larger volume sample, the light intensity must be increased. Since these systems are typically already using the most intense light sources practicable, a reduction in sample volume necessarily results in a reduction of optical power through the system and a corresponding reduction in the sensitivity with which the angular deflection of the light beam may be determined. A reduction in the sensitivity with which the angular deflection of the light beam may be determined corresponds directly to a reduction in sensitivity of the dRI measurement.

A third way by which reducing sample volume reduces sensitivity of the dRI measurement is once again due to a reduction in the area through which the light beam may be sent. As the area through which the light beam is sent is reduced, diffraction effects limit the sharpness with which the beam may subsequently be focused. The smaller the area through which the beam passes, the more diffuse the focal point becomes. Typically, a system used to measure the angular deflection of the light beam has its sensitivity increase as the sharpness of the focused beam increases. And so yet again reducing the area through which the light beam passes results in a decrease in sensitivity in determining the beam angular deflection, corresponding to a reduction in sensitivity of the dRI measurement.

Another consideration increases the sensitivity of the dRI as the sample volume is reduced. When samples of changing composition pass through the cell, as is the case when the detector is used as an online chromatography detector, the sample in the cell will be spatially inhomogeneous. This causes the cell chambers to act as weak lenses that can influence the shape of the spots on the focal plan. Unlike the previous consideration of the averaging of the dRI of the samples in cell, the sharpness of the spots is compromised along with the ability of finding their accurate positions. When the sample volume is decreased, this effect is minimized allowing for a more accurate determination of the spot position. This same consideration also applies to thermal inhomogeneities in the cell. As the flow cell volume is decreased, both the composition and temperature uniformity are improved.

It is an important objective of the parent invention, Ser. No. 10/768,600, to increase the sensitivity of a dRI measurement while at the same time minimizing the amount of sample required. Another objective of Ser. No. 10/768,600 is to reduce diffraction effects by increasing the dimension of the clear aperture through which the beam must pass without increasing the sample volume. A further objective is to provide for a broad range of instrument response without the beam moving too closely to any side of the cell.

The present invention, a continuation-in-part of Ser. No. 10/768,600, is concerned with enhancing further the sensitivity of Ser. No. 10/768,600 by improving the detection methods by which the angle of the emerging transmitted beam may be determined. Thus it is an objective of the new inventive detection methods described here to improve the precision of the determination of the angular displacement of the transmitted beam. Determination of the light beam deflection angle after passing through the fluid chambers is typically accomplished by measuring the light beam position on a plane surface some distance from the fluid containing chambers. Changes in the beam position on that plane may be related via trigonometric relations to changes in the angular deflection of the light beam. It is a further objective of this continuation-in-part to determine such angular deflection with greater precision. It is another objective of this invention to extend greatly the range of measurement of the said differential refractive index differences between the fluids of the special cells of the parent invention.

It is a further objective of this invention to eliminate the need to reposition the transmitted beam for each major change of refractive index difference. With a conventional split photodiode detector, over which the transmitted beam moves, once the beam has moved so that it illuminates only one section of the detector, the scale has reached its limit and the beam position must be reset. By mechanical means, the beam position is repositioned so that it once again illuminates both components of the split photodiode. Since the present invention permits response to an extremely broad range of differential refractive indices without need to reposition the beam, the present invention eliminates a significant moving part from the preferred implementation.

BRIEF DESCRIPTION OF THE INVENTION

In order to provide detection of a far greater range of refractive index differences, the traditional split photodiode detector is replaced by a photodetector array comprised of a plurality of detector elements. In addition, to improve further the precise detection of the translated beam falling on the photodetector array, the beam itself is replaced by a plurality of beams providing thereby a set of signals from the plurality of beams, each one of which generally covers a range of the many detector elements of the photodetector array. Each contributing beam, therefore, produces a set of signals indicative of its displacement and the plurality of beams produces a plurality of displacement signals which, when all combined and processed, results in a displacement determination of improved precision. From this displacement determination, the mean angular detection of the transmitted beams may be used to determine a highly precise measurement of the differential refractive index. Selectively inserting a negative lens into the emerging beam enhances further the precision by which the beam's angular deflection may be measured.

DETAILED DESCRIPTION OF THE INVENTION

The objective of all dRI detectors is to measure the refractive index difference between the reference and sample fluids. For a walk-off type dRI detector, this is accomplished by measuring the angular deflection of the light beam emerging from the cell after traversing it. The translation of the emerging beam relative to the incident beam contributes to limit the sensitivity of the conventional cell structure by reducing the region within the sample chamber which may be illuminated and still have that light reach and traverse the reference chamber. This translation has a major dependence upon the refractive index difference between the sample fluid refractive index and that of the transparent material of which the cell is fabricated, and a minor dependence on the refractive index difference between the sample and reference fluids. For most practical applications, especially those related to the field of liquid chromatography, the refractive index difference between the two fluids is small compared to that between the fluids and the cell material.

Figure 1:
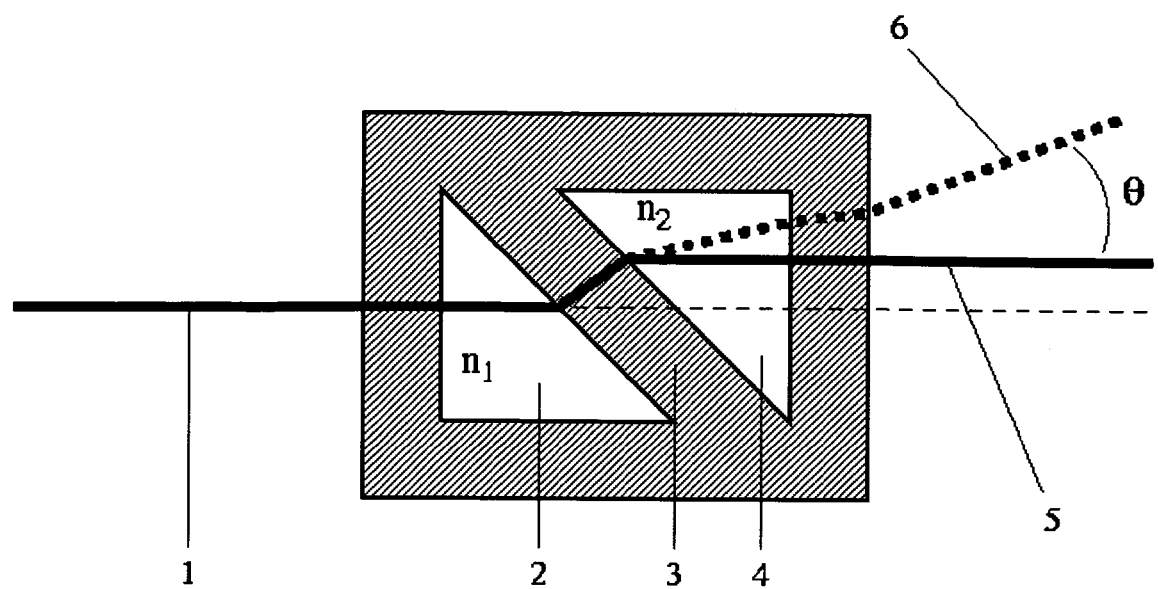
FIG. 1 shows a conventional dRI cell design illustrating the displacement of the transmitted beam.
Figure 2:
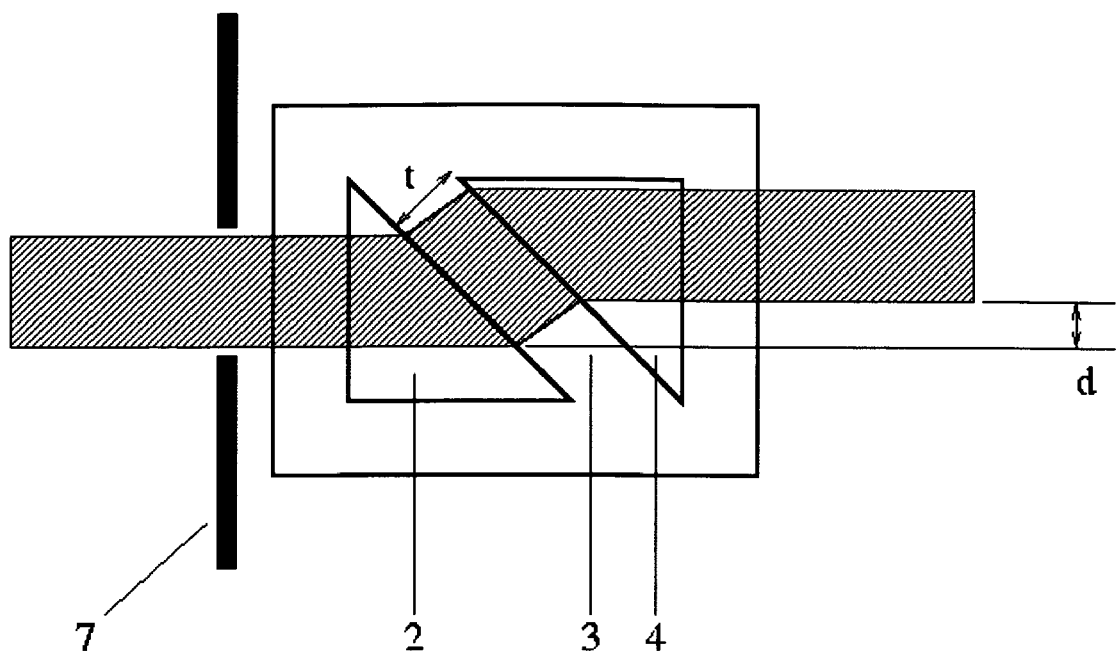
FIG. 2 shows a conventional cell with the beam filling most of the sample chamber.

FIG. 1 shows a very thin light beam for purposes of clarity. The cell when filled with as much light as possible, for the reasons discussed in the background section, is shown in FIG. 2. Note that the beam undergoes a translation d as it passes through the partition 3 of thickness t between the sample and reference chambers. That translation need not contribute to the dRI measurement, since using simple optics it is possible to separate angular deflection of the beam, shown as θ in FIG. 1, from its translation, indicated by d in FIG. 2. However, that translation does limit the volume within the sample chamber which may usefully be illuminated. Light near the edges of the sample chamber 2 could miss the reference chamber 4, and thus not contribute to the measurement, reducing, thereby, its sensitivity. If light is allowed to enter the sample chamber 2 that misses or grazes the reference chamber, it will reflect and scatter from various surfaces, corners, and discontinuities of the cell typically contributing, thereby, a spurious and undesirable signal to whatever device is measuring the angular deflection of the light beam. To prevent that situation, an aperture 7 is typically placed before the flow cell, as shown in FIG. 2, ensuring that light which would miss or graze the reference chamber 4 is not permitted to enter the sample chamber 2.

The direction of the translation depicted in FIG. 1 and in FIG. 2 is appropriate when the index of refraction of the fluid is less than the index of refraction of the material comprising the cell. That is the common case, but in some instances the fluid to be measured has a higher index of refraction than that of the cell material. For example, a fluid such as toluene has an index of refraction of 1.5 that is greater than a typical cell material made of fused silica, with an index of refraction of 1.46. Since dRI detectors are typically designed to operate with a variety of fluids, the aperture is made small enough and positioned such that, over the desired range of fluid refractive indices, no light will graze the reference chamber walls. For a typical low volume type flow cell, the light beam may be restricted to enter only the central 65% of the sample chamber 2; the rest of the chamber being essentially unused, but nevertheless filled with sample fluid. It is the thickness of the partition 3 that results in a translation of the light beam, and the negative consequences described above associated with that translation. As the thickness of the partition is brought to a negligible thickness, the translation goes to zero, as do the consequences associated with the grazed surfaces of the reference chamber 4. Additionally, when the thickness of the partition is decreased, the two fluids are brought into better thermal contact, reducing the undesirable effect of thermally induced changes in the refractive index. However, it is practically difficult to make that dimension small. Furthermore, as the partition dimension is reduced, pressure differences between the sample and reference chambers cause the partition between them to flex, adding noise and distortion to the measurement. Pressure differences inevitably exist between the sample and reference chambers, especially in the case where fluid is flowing through one or both chambers.

Figure 3:
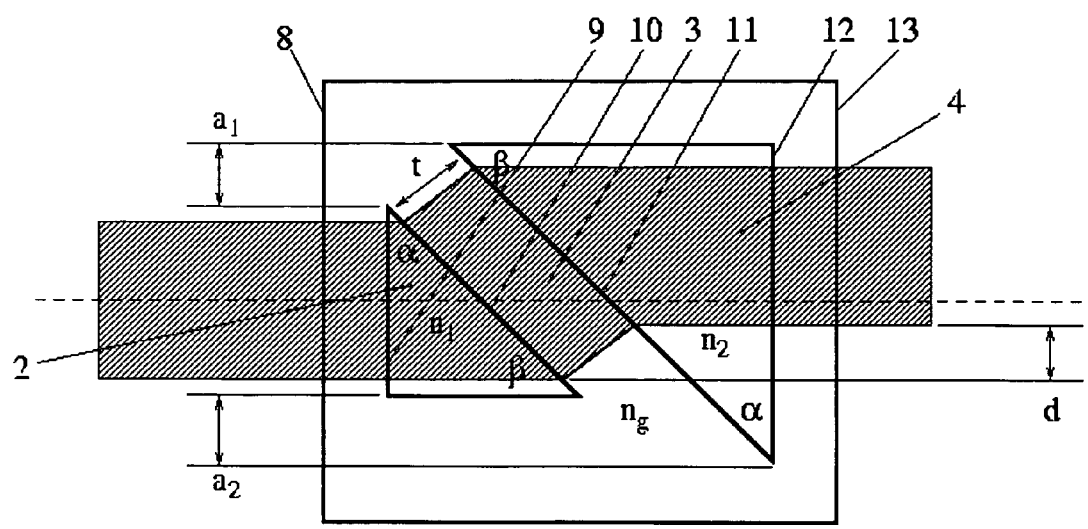
FIG. 3 shows a preferred embodiment cell of the present invention wherein the reference fluid chamber is larger than the sample fluid chamber.

The reference chamber 4 of the parent invention, whose preferred embodiment is shown in FIG. 3, is made sufficiently larger than the sample chamber to allow the light beam to traverse said reference chamber without impinging on any of its corners located at the intersections of said chamber's faces, nor grazing any side through which said beam is not intended to pass after said beam has entered the sample chamber 2 at any position along face 9, traversed the sample chamber, and passed onto and through the partition 3 into said reference chamber. This allows the full volume of the sample chamber to be illuminated by the incident beam. As the fraction of the sample chamber volume illuminated is increased, the sensitivity of the measurement is increased without increasing the size of the sample chamber. Conversely, using the invention described, the sample volume may be made smaller than in a symmetric flow cell with no loss in measurement sensitivity since, in the preferred embodiment, a greater fraction of the sample chamber volume is illuminated. For conventional chromatographic measurements, the reference chamber 4 is filled with a reference fluid at the beginning of a measurement and is kept constant during the course of the measurement. Thus an increase in volume of the reference chamber 4 does not affect the volume of the sample required for a measurement.

The degree by which the flow cell reference chamber 4 must be made larger than the sample chamber depends upon the physical details of the flow cell and the range of solvent refractive indices to be measured. For any embodiment, the reference chamber 4 must be made large enough and positioned correctly for the light incident anywhere in the sample chamber 2 to successfully reach and traverse the reference chamber. In FIG. 3 we show a preferred embodiment of the invention. In this embodiment, the reference chamber 4 has a triangular cross section which is a similar triangle to the sample cell cross section. The planes 8, 9, 12, and 13 are parallel to one another, and the planes 10 and 11 are parallel to one another. The sample and reference chambers are separated from one another by a partition of thickness t, and the light beam depicted is translated by a distance d due to passage through the partition. The fluid in the sample chamber has refractive index $n_1$, that in the reference chamber has refractive index $n_2$, and the partition between the sample and reference chambers has refractive index $n_g$. The refractive index difference between the sample and reference fluids $n_1$ and $n_2$ is typically of the order of $1 \times 10^{-3}$ or less, while that between $n_1$ or $n_2$ and $n_g$ is of the order of 0.1. For the purposes of simplifying the derivation below, we will assume $n_1 \approx n_2 \equiv n_1$. With this assumption, the translation d may be seen to be:

$$d = t \sin(\alpha) \left\{ 1 - \frac{m \cos\alpha}{\sqrt{1 - m^2 \sin^2\alpha}} \right\}, \text{ where } m = n_1 / n_g.$$

Note that in the case when the liquid has a higher refractive index than the transparent material of the cell, i.e. m>1, d is negative and the beam displacement is downward.

As discussed in the parent application, measurement of the deflection angle of a beam of light after the light has passed through the fluid containing chambers allows the measurement of the differential refractive index, dRI, between two fluids. An earlier application, Ser. No. 10/723,548 as listed on the first page of this specification, describes a flow cell which allows measurement of the dRI between two fluids or the absolute refractive index, ARI, of identical fluids contained in the two cells. The measurement of dRI or ARI is accomplished via measurement of the deflection angle of a beam of light after the light has passed through the fluid containing chambers. This latter measurement requires, in a preferred embodiment of the invention, that surface 12 be not parallel to surface 9. The present invention is directed to the determination of the deflection angle.

In the following discussion, we shall assume that the deflection angle is to be determined in order to measure dRI between two different fluids contained, respectively, in the two chambers 2 and 4 of FIGS. 2 and 3. The planes 12 and 9 of FIG. 3 are parallel. For the case of non-parallel planes 12 and 9, the ARI of identical fluids contained in the two cells may be determined as well from measurement of the deflection angle as described in detail in earlier referenced application Ser. No. 10/723,548.

Figure 4:
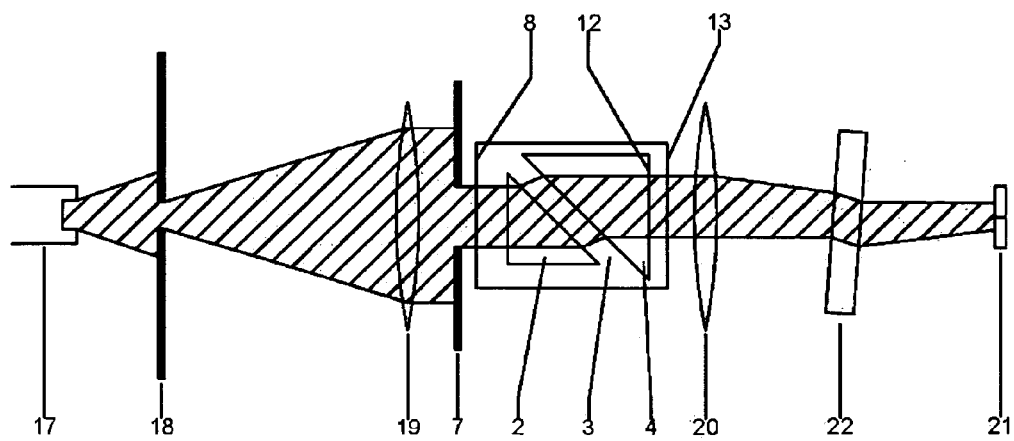
FIG. 4 shows a beam passing through the sample cell and falling on a split photodiode detector.

The principle technique employed to date by dRI instruments for the measurement of the light beam position has been to use a split photodiode, consisting of two photo sensitive elements side by side. A typical system using a split photodiode is shown in FIG. 4. In the system pictured, a light source, 17, illuminates a rectangular aperture, 18. That aperture is placed in the focal plane of a converging lens, 19, causing the light from the aperture to be collimated after passing through the lens. The collimated light is then restricted by means of an aperture, 7, to traverse the fluid containing chambers where it undergoes an angular deflection. The beam is then sent through a second converging lens, 20. Mirror means inserted immediately after the cell replacing lens 20 may be used to increase the paths through the solutions and have been discussed in the parent application. For the present specification the additional transmissions of the reflected beam caused thereby are not discussed as their use and implementation are familiar to those skilled in the art. An image of the rectangular aperture 18 will be formed in the focal plane of the second lens 20 which lies on a so-called split photodiode, 21, placed at that location.

Figure 5:
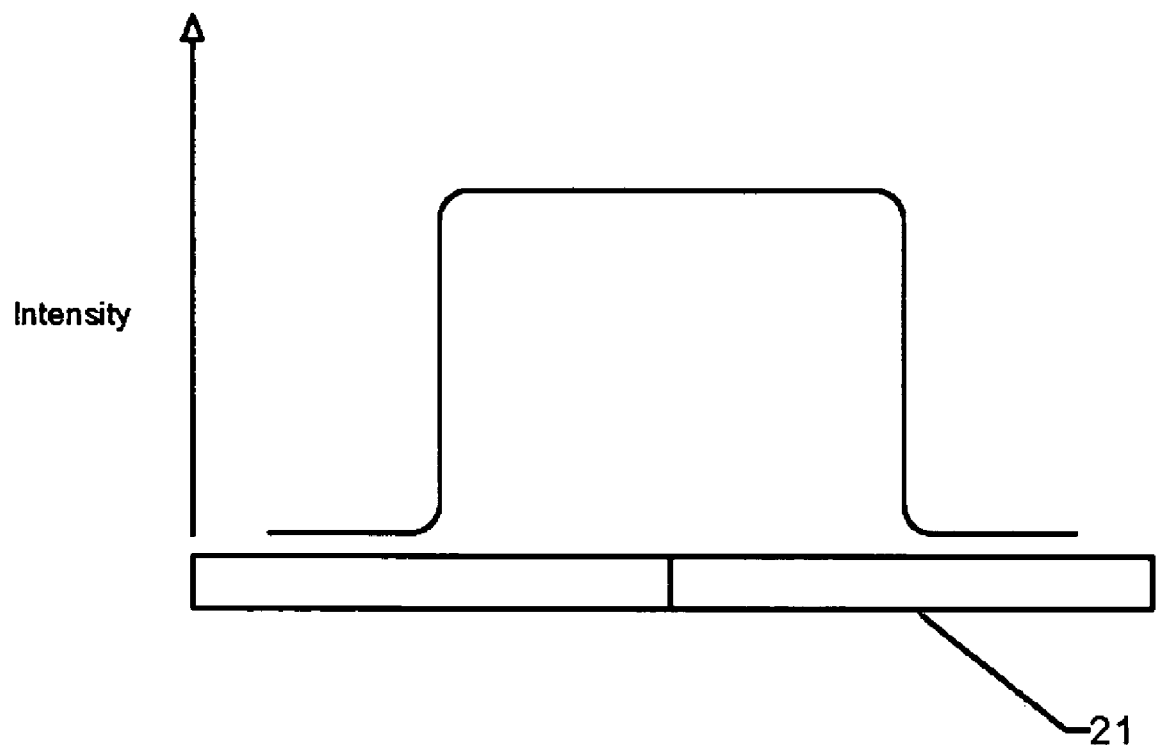
FIG. 5 shows the beam intensity profile relative to its position on the split photodiode.

The split photodiode 21 is comprised of two independent photodiodes whose individual signals are proportional to the amount of the transmitted image lying thereon. For a "zero" signal, the image of the rectangular aperture is translated by means of a glass plate 22 capable of rotation until the signals from the two photodiodes are identical. If the beam now undergoes an angular deflection due to a change in dRI, then the image position moves such that a larger portion of the image impacts upon the first photodiode element relative to the second photodiode element, and the relative signals change proportionally. For a rectangular image and spatially uniform independent photodiodes, the difference between the signals from the two diodes is, to first order, proportional to the angular deflection of the beam leaving the fluid chamber. Analog circuitry may be used to produce a voltage proportional to the difference between the two signals, and so the beam position and associated beam deflection angle may be measured. For a split photodiode system, the maximum signal which may be measured is limited by the dimensions of the photodiodes and the rectangular image. When the image moves completely off of the first detector and onto the second detector then it is no longer possible to determine the beam position. FIG. 5 shows the beam intensity profile with respect to the two photodiode elements at 21.

Figure 7:
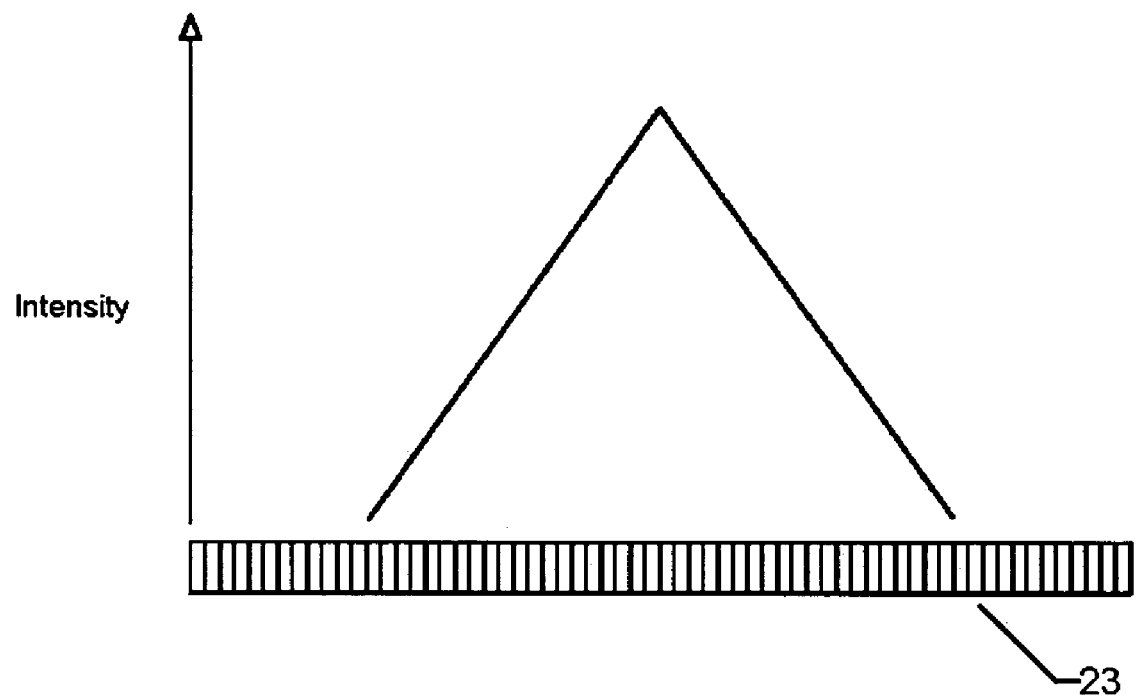
FIG. 7 shows a triangular intensity profile falling on a photodetector array.
Figure 8:
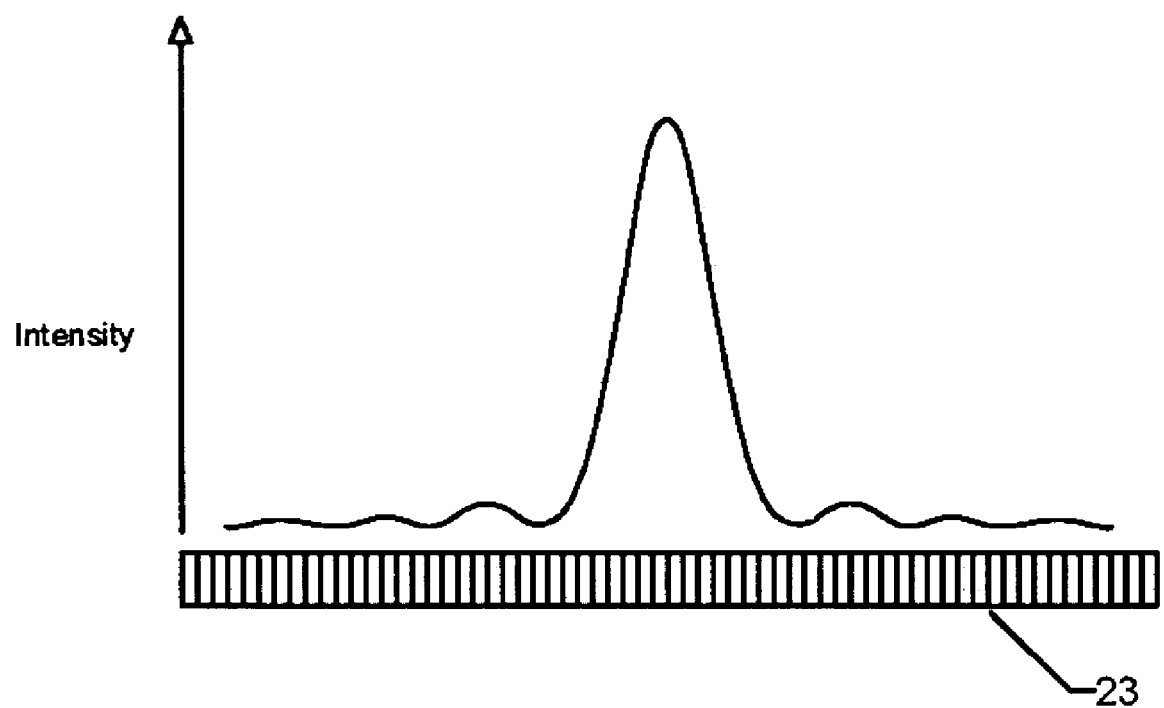
FIG. 8 shows a diffraction modified intensity profile falling on a photodetector array.

Rather than the double photodiode structure 21, our invention uses a plurality of photodetectors 23, such as a photodiode array or a charge coupled device array, for the measurement of the light beam position and the subsequent determination of the associated dRI, and ARI values. Note that determination of the location of the beam and, thereby, its effective angular displacement depends critically on only the few detectors near the edges of the beam as the intensities falling on the diodes between the edges are all the same. To improve the determination of the beam location by means of additional photo detectors, we need a greater beam intensity variation over a broad range of individual photodetector elements; such intensity variation providing additional means by which said intensity variation may be fitted analytically to improve thereby said beam location determination. FIG. 7 presents a simple triangular intensity variation whereby the photodetector elements spanned is broad and the relative variations of intensity detected by each element may be used to define more accurately the beam position. Referring back to FIG. 4, if the combination of apertures 18 and 7 be made small enough, the resulting beam profile will show intensity variations associated with diffraction limitations and produce an intensity variation such as show in FIG. 8. Again, beam intensity variations encompassing a broad range of photodetector elements permit a more accurate determination of the beam location.

Figure 9:
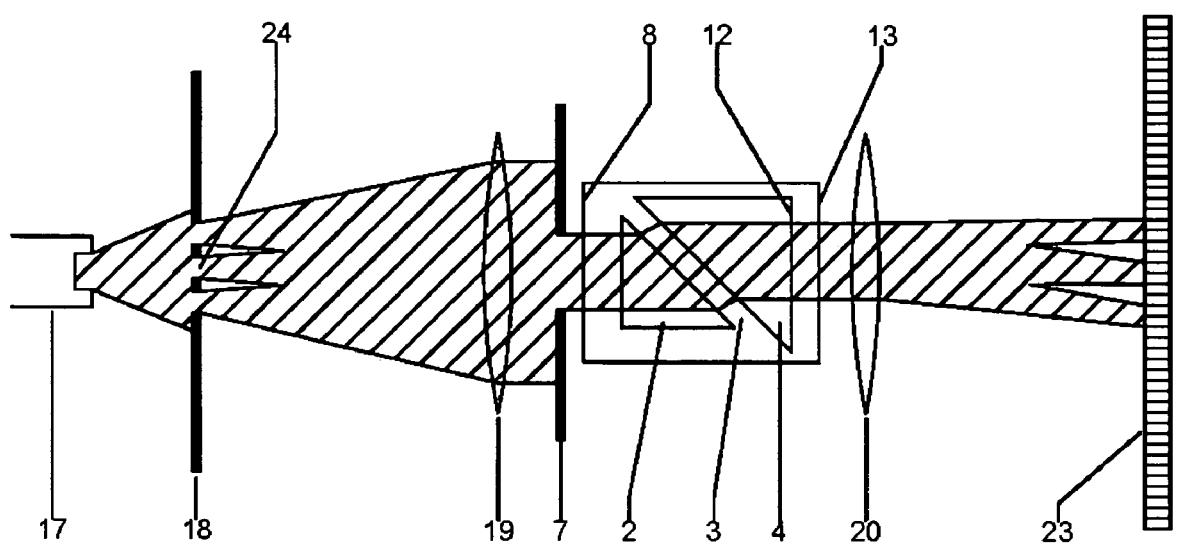
FIG. 9 shows the geometry of a set of beams passing through the sample cell and falling on the photodetector array.
Figure 10:
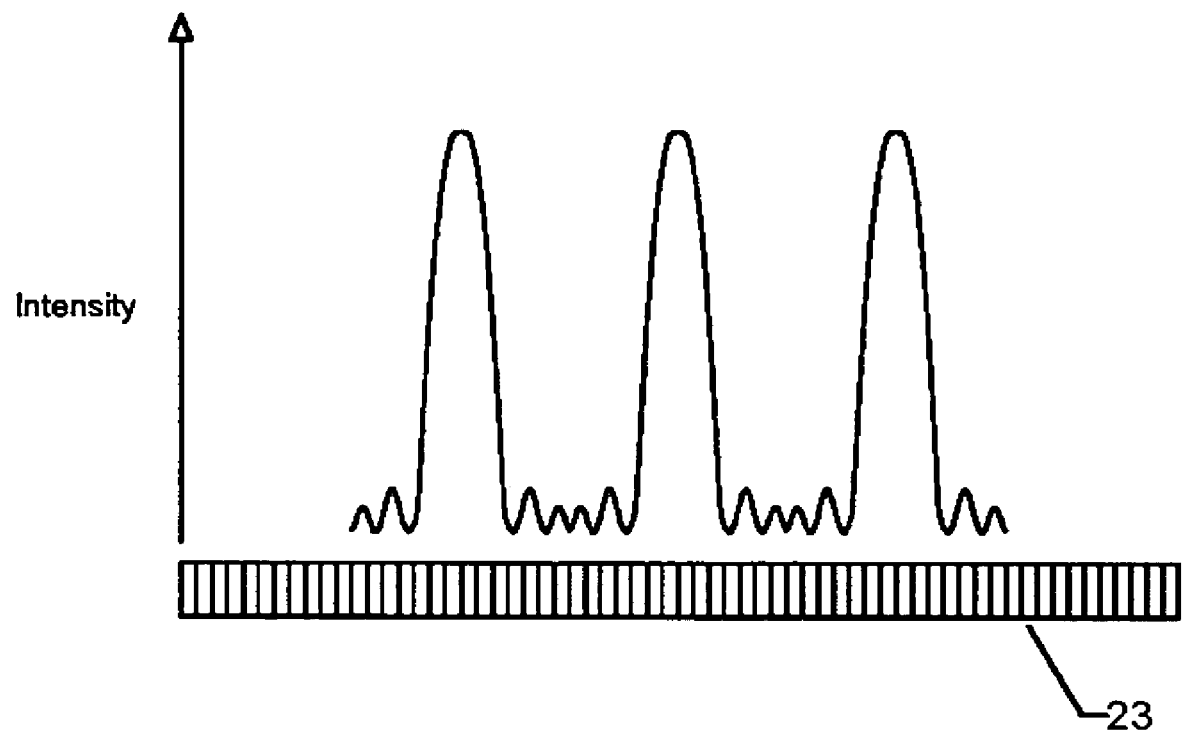
FIG. 10 shows a set of diffraction modified intensity profiles from the corresponding set of beams of FIG. 9 falling on a photodetector array.

Consider now the arrangement of FIG. 9 whereby the single beam incident upon the cell is replaced by a plurality of beams generated by means of an aperture 18 modified to contain a series of narrow apertures or slits 24 rather than a conventional single aperture. For the example illustrated in FIG. 9, the number of apertures selected was three. Similar to the case of the split photodiode system, the series of narrow apertures is placed in the focal plane of converging lens 19, causing the light from the apertures to be collimated after passing through the lens. The collimated light is then restricted further by means of aperture 7 to traverse the fluid containing chambers where it undergoes an angular deflection arising as a consequence of the refractive index difference of the fluids in the two chambers of the sample cell. The emerging beam is then sent through a second converging lens, 20. Diffraction limited images of the series of narrow apertures are formed in the focal plane of this second lens at the photodetector array, 23. FIG. 10 shows the intensity variation of the triple beam at it spans a broad range of the photodetectors. With a plurality of detectors and the ability to determine the position of the light beam on those detectors, or the average position of many light beams, it is possible to extend the range of the measurement and/or increase the sensitivity of the measurement. Additional beams may be created to yield patterns covering even more detectors. This could be achieved by using more apertures 24 in the mask to create additionally complex and, thereby, more easily defined intensity variations.

Consider, as an example, using a 512 element photodiode array. With this unit, it is possible to increase the dynamic range of the measurement, defined as the largest measurable signal divided by the system noise, by a factor of 50 over conventional split photodiode instruments. Such an increase in the measurement dynamic range is clearly of great utility in many settings. With a large range of detection elements it is also possible to eliminate the use of the rotating glass plate 22 as shown in FIG. 4, since small translations of the light beam are not relevant to the measurement of its angular direction. The starting position of the light beam on the photodetector array may simply be considered the "zero" position, without that position being at the center of the array. The elimination of moving parts is always desirable in any measurement system, since such moving parts tend to add complexity and additional routes to system failure.

Figure 6:
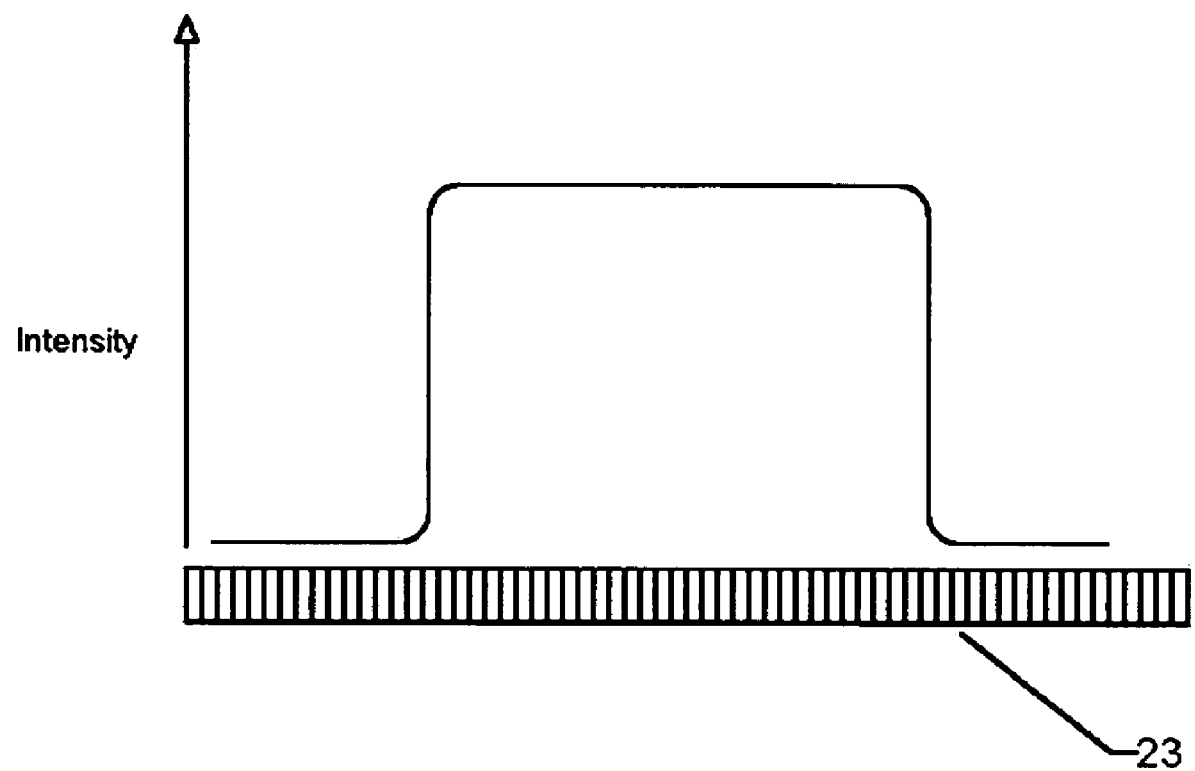
FIG. 6 shows the intensity profile of a beam falling upon an array of photodetector elements.

With a plurality of photodetectors one must use more advanced mathematical techniques, such as fitting to some functional form the photodetector response as a function of detector position, to determine accurately the mean light beam position on the photodetector array. Such functional fitting techniques can enhance greatly the precision by which the light beam position may be determined. Additional enhancements to the precision with which the light beam position may be determined may be gained by tailoring the light beam to have a specific profile. For example, a light beam with a sharply peaked profile such as shown in FIG. 7 allows a better determination of the light beam position than does a flat-topped function, such as the square pulse function used in typical split photodiode systems arising from the image of a rectangular aperture as shown in FIGS. 5 and 6. With a light beam profile that is a perfectly flat-topped square pulse function it is generally possible to determine the beam position using intensity thresholds or similar means, but the two photodetectors at the two edges of the beam are the only photodetectors which can contribute to knowledge of the position of the light beam to a resolution of less than the width of a single photodetector element.

The ideal width of a peaked function depends upon the noise in the measurement of the photodetector response. As noise levels increase, the ideal width of the peaked function with respect to the physical dimension of the photodetector elements must be increased to allow better averaging. In addition to a single peaked function, it is possible to introduce a large number of other functional forms for the light beam profile which will enhance the sensitivity of measurement. For example, if the light beam profile is made to have multiple peaks such as shown in FIG. 10, each peak will contribute to the determination of the mean beam position. For "white" measurement noise, the precision with which the beam position may be determined increases as the square root of the number of peaks. Yet another light beam profile which could be used to enhance the precision of measurement would be a sinusoidal or a triangle-wave profile having many periods. In general, maximizing the number of detectors which have a large change in signal from their neighboring detectors maximizes the precision with which the beam position may be determined. While an extended array of peaks, such as a sinusoidal profile, provides an increase in the sensitivity of the measurements due to increased averaging, it adds the complication that it is in general impossible to distinguish between the pattern and one translated by an integral multiple of sinusoidal peaks, unless the pattern moves slowly enough that the motion of the pattern can be tracked. With a finite array of peaks, one achieves the improved averaging of multiple peaks, without the degeneracy of the periodic array.

It is important to stress that our inventive method makes use of a photodetector array and, in one of its preferred embodiments, a plurality of beams as a means for improving the determination of the position of said beams. This is in contradistinction to the use of similar elements in, say, an Abbe absolute refractometer. Modern Abbe type ARI instruments often incorporate a detector array with multiple beams of light falling on it at fixed positions. The multiplicity of illuminated elements in those instruments is used to determine the intensity of the illumination by those fixed beams. In our invention, the multiple beams are moving and the multiplicity of illuminated elements is used to improve our measurement of the position of the beams.

The light beam profile falling on the detector array may be tailored in a number of ways. One means by which the light beam profile falling on the photodetector array may be tailored is by providing a complex object that is imaged at the photodetector array. In the case of FIG. 9, the series of narrow apertures 24 at the mask 18 are objects that are imaged on the photodetector array, producing a pattern of light such shown as FIG. 10 that will enhance the precision by which the mean light beam position may be determined. The object to be imaged on the photodetector array need not be limited to simple apertures, but may also consist of light transmitted through or reflected from a transparent medium with an opaque pattern partially obstructing or partially reflecting the light. For example, a sinusoidal ink density variation may be printed onto a clear plastic or glass sheet for use as the apertures 24 in FIG. 9. Light incident on that aperture will create a complex object imaged at the photodetector array plane 23.

An additional way to tailor the light beam profile is to create an image at a plane displaced from the photodetector array plane. Such a displaced image results in an unfocused image on the photodetector array, effectively smoothing the pattern of light. For example, if the object consists of a series of narrow apertures whose image at the photodetector plane would appear as a series of sharp flat topped peaks, by imaging those apertures at a plane slightly in front of or behind the photodetector array plane, then the light pattern on the array would consist of a series of peaks somewhat resembling those in FIG. 10.

Diffraction effects also may be used to tailor a light beam profile. Any object which is imaged after passage through aperture 7 will be modified due to diffraction effects of said aperture. The image will be a convolution of the actual object with the corresponding aperture function of 7. For example, if aperture 7 is rectangular with width b, then the image will be the convolution of the object with the well-known sinc function squared (cf. Hecht, *Optics*, Addison-Wesley, Reading, Mass., 1974):

$$I(\varphi) = I(0)\frac{\sin^2\beta}{\beta^2} \text{ with } \beta = \frac{2\pi}{\lambda}\frac{b}{2}\sin\varphi$$

where $\lambda$ is the wavelength of light used for the measurement and $\phi$ is the deflection angle from the central position angle of the beam of light.

In general, any aperture function is a peaked function whose width is determined by the width of aperture 7, the distance from lens 20 to the image, and the wavelength of light used. If the image produced is large compared to the width of the aperture function, such as the image of aperture 18 on the split photodiode 21 in the split photodiode system of FIG. 4, then diffraction will produce only a minor relative modification of the intensity image shown in FIG. 5. If, however, the image has dimensions which are very small compared to the width of the aperture function, then the image will be dominated by the aperture function. For example, if the aperture is made to be an extremely narrow slit, then the image will simply be the diffraction pattern shown in FIG. 8. In the absence of diffraction effects, an array of narrow apertures 24 in FIG. 9 would image at the photodetector array as a series of perfectly flat-topped square pulse functions. However, if the size of aperture 7 is small, then the image at the photodetector would be a series of peaked functions corresponding to the convolution of the function $I(\phi)$ with the narrow flat-topped square pulse functions. By tailoring the dimensions of aperture 7, the dimensions of the slits 24, the distance from lens 20 to the image, and the wavelength of the light used for the measurement, it is possible to modify the image to be more or less peaked.

The split photodiode system and the invention using a plurality of photodetectors both determine the position of the light beam in a plane and use trigonometric relations to relate that position to an angular deflection $\theta$ of the light beam emerging from the fluid containing chambers. For the case of the plane of detection oriented exactly perpendicular to the path of the undeflected light beam, as pictured in FIGS. 4 and 9, the beam deflection angle $\theta$ of FIG. 11 with respect to the direction of the incident beam is related to the spatial displacement $x_1$ of the beam at the plane of detection as $x_1 = L \tan(\theta)$, where L is the distance from the imaging lens 20 to the plane of detection 23. For a given angular deflection $\theta$, the distance $x_1$ which the beam moves increases as the distance L increases. An increase in $x_1$ with increasing L for a given $\theta$ is generally true regardless of the orientation of the detection plane with respect to the path of the undeflected light beam. For a given precision with which the position of the light beam may be determined, the sensitivity in the measurement of the angular deflection θ may be increased by increasing the distance L. To obtain better precision in the determination of θ, L must be made as large as is practically possible. However, there are numerous deleterious effects associated with a very large dimension L. In general, the spatial position of the light beams in these systems often must be determined to a fraction of a nanometer, and so both thermal and mechanical stability of the optical systems is of paramount importance. Thermal and mechanical stability are inevitably degraded as the physical dimensions of the system are made larger. However, using an additional diverging lens, it is possible to increase the effective optical length of the system without increasing the physical length.

Figure 11:
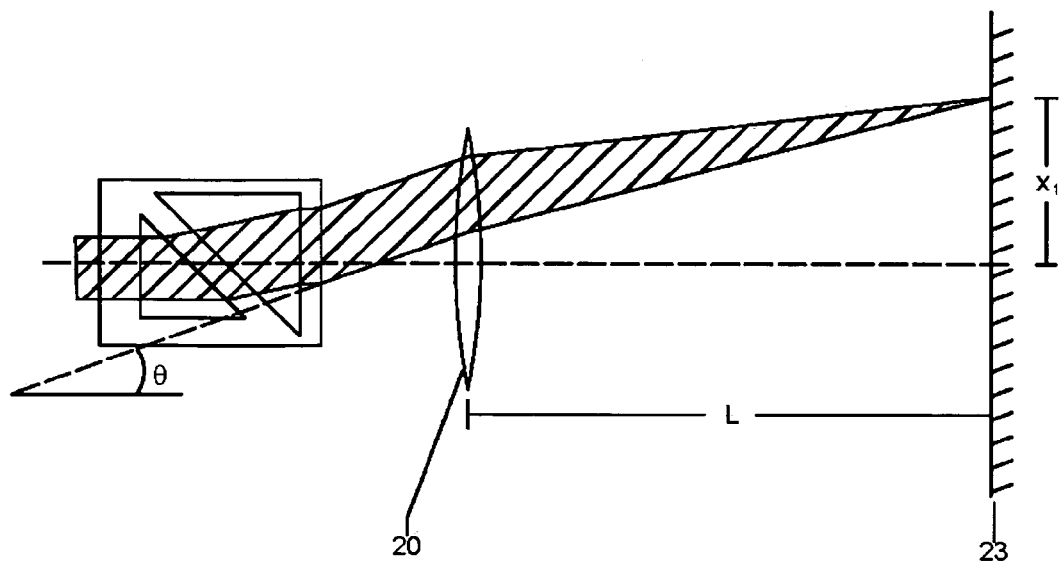
FIG. 11 shows the angular deflection of a beam emerging from the cell and then an imaging lens producing a corresponding displacement $x_1$ along the array.
Figure 12:
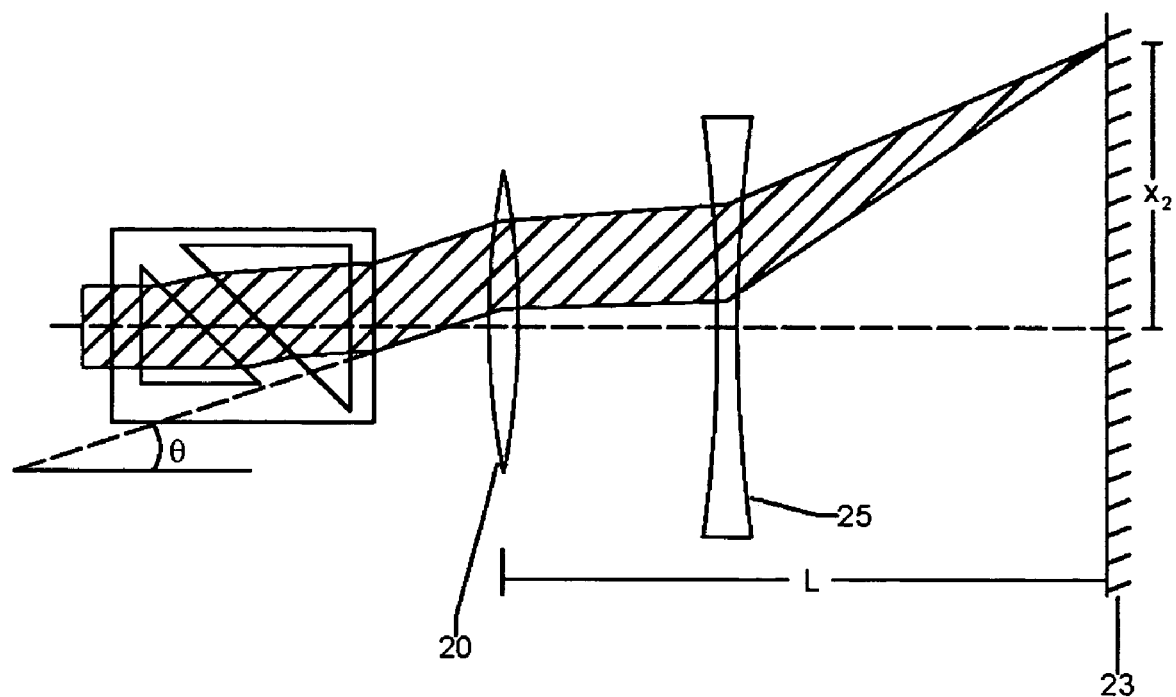
FIG. 12 shows the angular deflection of a beam emerging from the cell, an imaging lens, and an added negative lens producing a corresponding displacement $x_2$ along the array.

FIG. 11 shows the standard configuration with a single beam emerging from the flow cell at an angle θ with respect to the cell exit face 13 and entering the imaging lens 20 located at a distance L from the plane of the detector array 23. The beam falls on the detector array at a distance $x_1$ from the effective zero position of the beam, where $x_1 = c_1 \tan(\theta)$ and $c_1$ is a constant. Inserting a negative lens 25 in the path following the collimating lens 20, as shown in FIG. 12, forms a virtual image of the source increasing, thereby, the beam displacement along the detector array 23 shown as the distance $x_2$, where $x_2 = c_2 \tan(\theta)$ and $c_2 > c_1$. The determination of the angle θ is thus made more precise since this lens has effectively produced a result corresponding exactly to that which would be produced by a longer path L without any of the detrimental effects of such an increase.

Although much of the discussion concerning the use of an array of photodetectors to enhance and improve the performance of a differential refractive index detector has focused on a single passage of the beam or beams through the flow cell, it should be emphasized that the sensitivity of our device will be improved by the familiar method of inserting a mirror that would reflect the beam back through the cell, as disclosed in the parent application. For this implementation, the source beam would be incident on the flow cell at a slight angle to the surface 8 shown in FIG. 3. The photodetector array would lie, therefore, on the incident side of surface 8 positioned appropriately so as to miss the incident beam.

The examples throughout most of this specification have focused on implementations of the invention for differential refractive index detectors, dRI, while an earlier application disclosed the means by which the absolute refractive indices of fluids might be measured as well. A preferred use of the present invention would incorporate it into structures capable of making both such measurements as disclosed in these earlier applications.

There are many embodiments of our invention that will be obvious to those skilled in the art of differential refractive index measurements that are but simple variations of our basic invention herein disclosed. Accordingly,

We claim:

1. An improved differential refractometer to measure the refractive index difference between a sample and reference fluid comprised of
    a) A mask (18) restricting an incident light beam (1) produced by a light source (17) to fall onto a collimating lens (19) that produces a parallel beam of light falling on an aperture (7), said aperture restricting the cross section of said emerging beam before said beam is incident on the entrance face (8) of
    b) A measurement cell, said restricting aperture limiting said emerging parallel light beam to illuminate sample solution contained in said sample chamber (2) of said flow cell;
    c) A transparent partition (3) through which said parallel light beam passes, after having traversed said sample chamber (2), into
    d) A reference chamber (4) containing a reference fluid and bounded by said transparent partition (3) separating said sample chamber (2) from said reference chamber (4);
    e) A lens element (20) forming an image of said beam restricting mask (18) onto a
    f) A plurality of photo detector elements (23) each of width small compared to the diameter of the width of said mask (18) image at the plane of the photodetector elements such that several of said detector elements are illuminated by said mask (18) image; the measurement of the position of said mask image being improved by reference to the detected intensity variation across said plurality of illuminated detector elements.

2. The improved differential refractometer of claim 1 where said incident light beam is monochromatic.

3. The improved differential refractometer of claim 1 where said light source is a laser.

4. The improved differential refractometer of claim 1 where said light source is a light emitting diode.

5. The improved differential refractometer of claim 1 where said sample and reference chambers are of identical right triangular cross sections.

6. The improved differential refractometer of claim 1 where said sample and reference chambers are of similar right triangular cross sections with said beam restricting aperture (7) restricting said incident parallel beam to illuminate fully said sample solution contained in said sample chamber (2) of said flow cell without impinging sides nor grazing corners between defining sides of said sample chamber nor sides and corners of said reference chamber (4).

7. The improved differential refractometer of claim 6 where said reference chamber (4) is fabricated of adequate dimensions to insure that said entering parallel light beam does not graze other surfaces or corners therein before leaving said measurement cell irrespective of refractive index difference between reference and sample fluids.

8. The measurement cell of said improved differential refractometer of claim 7 where said adequate dimensions of said measurement cell are determined by calculation based upon said refractive index of said flow cell and the complete range of sample and reference refractive indices for which said improved differential refractometer will be used.

9. The measurement cell of said improved differential refractometer of claim 7 where said adequate dimensions of said measurement cell are determined by direct measurement of said transmitted beams for all sample and reference fluids for which said improved differential refractometer will be used.

10. The improved differential refractometer of claim 1 where said mask (18) is comprised of a single slit of dimensions small enough to insure that its image falling on said photodiode array (23) after passage through aperture (7) and said sample and reference chambers is diffraction limited insuring thereby that said image is substantially the aperture function of aperture (7).

11. The improved differential refractometer of claim 1 where said mask (18) is comprised of a plurality of slits (24) producing thereby a plurality of parallel beams incident upon said measurement cell and a plurality of transmitted images falling upon said photodiode array (23).

12. The improved differential refractometer of claim 1 where the internal entrance surface (9) of said sample chamber and the internal exit surface (12) of the reference chamber are not parallel to each other.

13. The improved differential refractometer of claim 1 where fluid contact surfaces, (10) and (11), of said transparent partition (3) are not parallel to each other.

14. The improved differential refractometer of claim 1 where said entrance face (8) of said measurement cell is not normal to said incident beam.

15. The improved differential refractometer of claim 13 where said non-normal incident beam transverses said measurement cell and is reflected back through said measuring cell by a mirror element means replacing said image forming lens element (20), said reflected beam emerging through entrance surface (8) at sufficient angle thereto to be detected by a photo diode array sufficiently displaced from said beam restricting mask (18) so as not to affect nor interfere with incident beam restricted thereby.

16. The improved differential refractometer of claim 15 where a negative lens (25) is inserted in front of said detector array (23) increasing, thereby, the virtual displacement of measurement cell transmitted beam with respect to direction of incident beam (1).

17. The improved differential refractometer of claim 1 where a negative lens (25) is inserted in front of said detector array (23) increasing thereby the virtual displacement of measurement cell transmitted beam with respect to direction of incident beam (1).

18. The improved differential refractometer of claim 1 where said plurality of photodetector elements are elements of a photodiode array.

19. The photodiode array of claim 18 where the number of elements is 512.

20. The improved differential refractometer of claim 1 where said plurality of photodetector elements are elements of a charge coupled device.

21. A method to measure the refractive index difference of a sample fluid relative to a reference fluid comprising the steps of
    a) Inserting a mask (18) into an incident light beam (1) produced by a light source (17) to restrict it to fall onto a collimating lens (19) that produces a parallel beam of light falling on an aperture (7), said aperture further limiting the cross section of said emerging beam before entering the entrance face (8) of a measurement cell containing two contiguous chambers (2) and (4);
    b) Placing a sample fluid and a reference fluid, respectively; into said contiguous chambers (2) and (4);
    c) Restricting, by said aperture (7) said emerging parallel beam to illuminate fully sample solution contained in said sample chamber (2) of said flow cell;
    d) Inserting into the path of the transmitted beam emerging from said measurement cell after traversing said sample and reference fluid containing chambers a lens element (21) forming an image of said beam limiting mask (18) onto a plurality of photo detector elements (23) upon which the transmitted beam falls; and
    e) Measuring the displacement of said transmitted beam using all the elements of said plurality of photodetectors that are illuminated by said transmitted beam relative to said transmitted beam's position when both said sample and reference chambers are filled with said reference fluid, the precision of said measurement being improved by reference to the detected intensity variation across said plurality of illuminated detector elements.

22. The method of claim 21 where said incident light beam is monochromatic.

23. The method of claim 21 where said light source is a laser.

24. The method of claim 21 where said light source is a light emitting diode.

25. The method of claim 21 where said sample and reference chambers are of identical right triangular cross sections.

26. The method of claim 21 where said sample and reference chambers are of similar right triangular cross sections with said beam restricting aperture (7) restricting said incident parallel beam to illuminate fully said sample solution contained in said sample chamber (2) of said flow cell without impinging sides nor grazing corners between defining sides of said sample chamber nor sides and corners of said reference chamber (4).

27. The method of claim 26 where said adequate dimensions of said measurement cell are determined by calculation based upon said refractive index of said flow cell and the complete range of sample and reference refractive indices for which said improved differential refractometer will be used.

28. The method of claim 27 where said adequate dimensions of said measurement cell are determined by direct measurement of said transmitted beams for all sample and reference fluids for which said improved differential refractometer will be used.

29. The method of claim 21 where said reference chamber (4) is fabricated of adequate dimensions to insure that said entering parallel light beam does not graze other surfaces or corners therein before leaving said measurement cell irrespective of refractive index difference between reference and sample fluids.

30. The method of claim 21 where said mask (18) is comprised of a single slit of dimensions small enough to insure that its image falling on said photodiode array (23) after passage through said sample and reference chambers is diffraction limited insuring thereby that said image is a diffraction image of said mask.

31. The improved differential refractometer of claim 21 where said mask (18) is comprised of a plurality of slits (24) producing thereby a plurality of parallel beams incident upon said measurement cell and a plurality of transmitted images falling upon said photodiode array (23).

32. The method of claim 21 where said reference chamber exit surfaces (12) and (13) are plane surfaces that are not parallel to each other.

33. The method of claim 21 where said entrance face (8) of said measurement cell is not normal to said incident beam.

34. The method of claim 33 where said non-normal incident beam transverses said measurement cell and is reflected back through said measuring cell by a mirror element means replacing said image forming lens element (20), said reflected beam emerging through entrance surface (8) at sufficient angle thereto to be detected by a photo diode array sufficiently displaced from said beam restricting mask (18) so as not to affect nor interfere with incident beam restricted thereby.

35. The method of claim 34 where a negative lens (25) is inserted in front of said detector array (23) increasing thereby the virtual displacement of measurement cell transmitted beam with respect to direction of incident beam (1).

36. The method of claim 21 where a negative lens (25) is inserted in front of said detector array (23) increasing thereby the virtual displacement of measurement cell transmitted beam with respect to direction of incident beam (1).

37. The method of claim 21 where said plurality of photodetector elements are elements of a photodiode array.

38. The photodiode array of claim 37 where the number of elements is 512.

39. The method of claim 21 where said plurality of photodetector elements are elements of a charge coupled device.

* * * * *